United States Patent [19]

Sano et al.

[11] Patent Number: 4,719,576
[45] Date of Patent: Jan. 12, 1988

[54] APPARATUS FOR MEASURING THE DEGREE OF ENTANGLEMENT IN A YARN

[75] Inventors: Takao Sano; Toshihiko Oka, both of Moriyama; Masafumi Ogasawara, Otsu, all of Japan

[73] Assignee: Toray Industries, Inc., Tokyo, Japan

[21] Appl. No.: 883,250

[22] Filed: Jul. 8, 1986

[51] Int. Cl.$^4$ .......................... G06F 15/46; G01L 5/04
[52] U.S. Cl. ...................................... 364/470; 57/264; 73/160
[58] Field of Search .................. 364/470, 550, 551; 73/159, 160; 57/264, 265, 284, 81

[56] References Cited

U.S. PATENT DOCUMENTS

| | | | |
|---|---|---|---|
| 4,116,393 | 9/1978 | Inouye et al. | 73/160 X |
| 4,133,207 | 1/1979 | Weidmann et al. | 73/160 |
| 4,148,178 | 4/1979 | Raschle | 73/160 X |
| 4,165,638 | 8/1979 | Verlin | 73/160 |
| 4,584,875 | 4/1986 | Woo et al. | 73/160 |
| 4,648,054 | 3/1987 | Farah et al. | 73/160 X |

*Primary Examiner*—Joseph Ruggiero
*Attorney, Agent, or Firm*—Birch, Stewart, Kolasch & Birch

[57] ABSTRACT

Between a feed roll feeding an entangled multifilament yarn to a measuring zone of degree of entanglement and a yarn-forwarding roll forwarding the yarn out of the measuring zone are disposed a first tension roll with a weight attached thereto, a pulley connected to a rotation meter and supported free to rotate, and a second tension roll with a weight attached thereto. A needle capable of piercing the yarn is provided between the pulley and either one of the first and the second tension rolls. Under the state wherein the needle pierces the yarn, an auxiliary weight is added to the first or the second tension roll, and the movement distance of the yarn from the position where the needle pierces the yarn to the position where the point of entanglement is engaged with the needle is measured by detecting the amount of rotation of the pulley. Next, the auxiliary weight is removed, an auxiliary weight is added to the other tension roll, and the movement distance of the yarn from the above position to the position where another point of entanglement is engaged with the needle is measured similarly.

The measured movement distance of the yarn corresponds to the distance between the points of entanglement and gives a measure of the entanglement. By the measuring apparatus, the degree of entanglement in a yarn can be measured automatically with high accuracy without using a tension meter.

20 Claims, 23 Drawing Figures

FIG. 16
FIG. 17
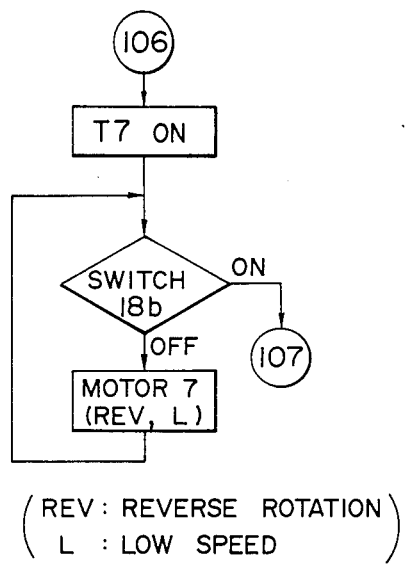
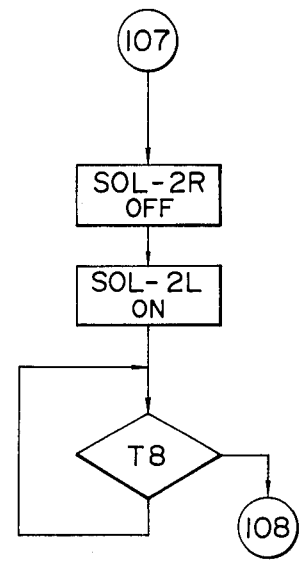
FIG. 18
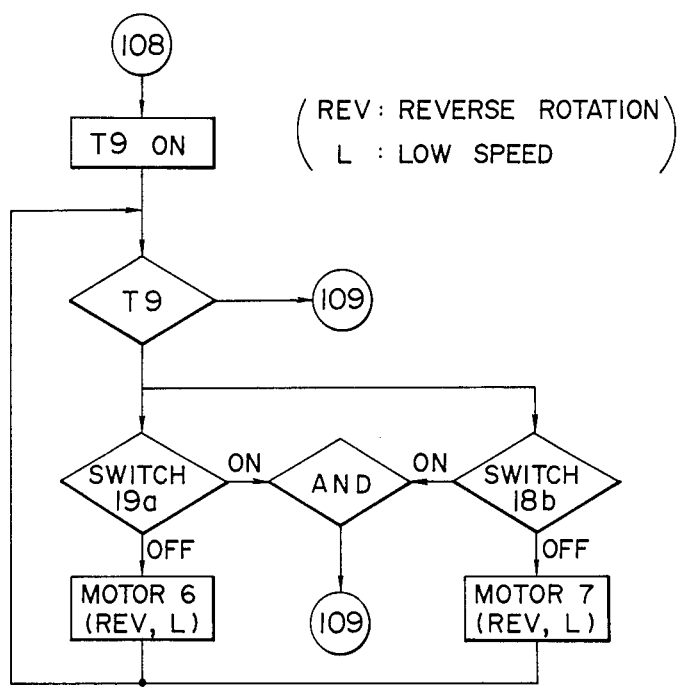

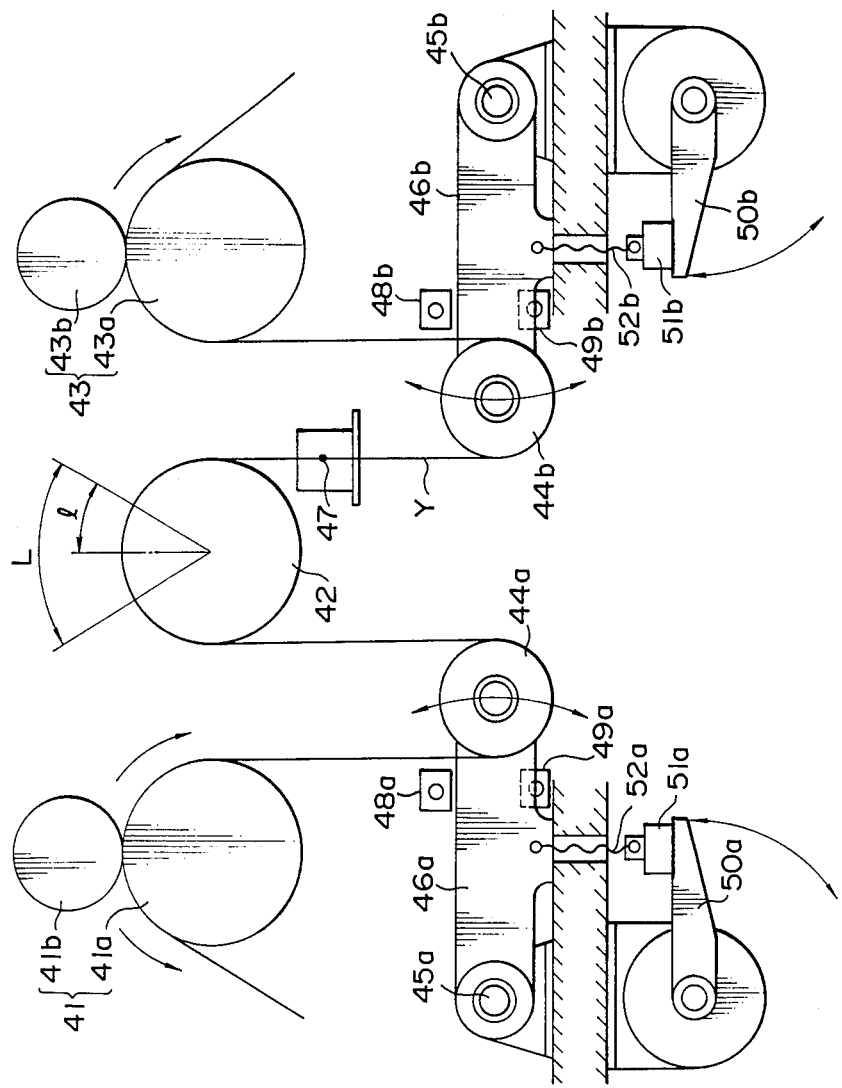

APPARATUS FOR MEASURING THE DEGREE OF ENTANGLEMENT IN A YARN

BACKGROUND OF THE INVENTION

1. Field of the Invention

The present invention relates to an apparatus for measuring the degree of entanglement in an entangled multifilament yarn.

2. Description of the Prior Art

As a method for giving cohesion to a multifilament yarn, a method for giving entanglement to single filaments which constitute a multilfilament yarn instead of giving twist is known. Since the entanglement in a multifilament yarn is easily obtained by disposal of the yarn in a turbulent flow of pressurized fluid such as compressed air, entangled multifilament yarns and apparatuses for their production are widely adopted in the textile industry. To indicate the degree of cohesion of a multifilament yarn due to such entanglement, a measure, generally called the degree of entanglement, is widely used.

Various methods for measuring the degree of entanglement in a multifilament yarn have been proposed. Of the conventional methods, one using the hook-drop test, such as the method disclosed in U.S. Pat. No. 2,985,995, is not only one of the most popular methods, but one of the best methods for measuring the pitch of points of entanglement (the length of opening) and the strength of entanglement.

This Hook-drop method is a method, wherein a hook with a weight is inserted through a multifilament yarn, and the degree of entanglement is determined on the basis of the distance through which the hook falls along the yarn on account of the weight of the hook.

The methods for performing automatically such measurement of the degree of entanglement due to Hook-drop method have been proposed from the view point of decreasing the measuring manpower, for instance, the method disclosed in U.S. Pat. No. 3,290,932 and the method disclosed in JP-A No. 52-53049.

However, there are several problems in such methods for measuring automatically the degree of entanglement. That is, there is the problem that a high performance and expensive tension meter is required to measure with high accuracy, whereby disadvantage on cost occurs, the problem that calibration of a tension meter is necessary, so that measurement takes a long time to measure, and the problem that errors may occur due to drift of the tension meter.

On the other hand, a method not needing a tension meter is disclosed in JP-A No. 58-115170. In this method, as shown in FIG. 23, a rotation meter 202 is connected to a pulley 201 which is free to rotate, and a needle 203 pierces the multifilament yarn Y threaded on the pulley 201. Weights 204a and 204b with a hook are hung respectively over the yarn Y positioned at both sides of the pulley 201, and electromagnets are built in the weights 204a and 204b respectively. Under the weights 204a and 204b, weights 206a and 206b constructed of magnetic material are provided, and the weights 206a and 206b are carried by carrying means 205a and 205b capable of moving in the vertical direction. Then, under the state of piercing the needle 203 into the yarn Y, the weights 206a and 206b are attracted to the weights 204a and 204b in turn, the yarn Y is moved in both directions over the pulley 201, and thereby the degree of entanglement of the yarn Y is determined.

However, in the above method, since it is necessary to place the weights 206a and 206b at a position under the weights 204a and 204b such that there is no interference with the vertical movements of weights 204a and 204b, enlargement of the apparatus in a vertical direction can not be prevented. Moreover, there is the problem, that it is rather difficult to stop the weights 206a and 206b always within the sphere of magnetic attraction of the electromagnets without contacting with weights 204a and 204b, in spite of change of the settled positions of weights 204a and 204b in accordance with the pitch of points of entanglement (the length of opening) in the multifilament yarn Y. For instance, in the condition wherein two weights 204a and 204b with a hook are balanced at both sides of the pulley 201 under the state of hanging the weights 204a and 204b, if the weight 206a or 206b having been carried upwards collides with one of the weights 204a and 204b, the weight 204a and 204b becomes unbalanced by reaction due to the collision, and the weight 204a or 204b may be raised to a position outside of the magnetic attraction. In that case, the weight 206a or 206b can not be attracted to the weight 204a or 204b, and the measurement of the degree of entanglement can not be continued.

SUMMARY OF THE INVENTION

An object of the present invention is to provide an apparatus for measuring the degree of entanglement in a multifilament yarn, which can be compactly designed and compact in use.

Another object of the present invention is to provide an apparatus for measuring the degree of entanglement in a multifilament yarn, capable of measuring with high accuracy.

A further object of the present invention is to provide an apparatus for measuring the degree of entanglement in a multifilament yarn, which can be compactly designed and compact in use.

To accomplish the above objects, an apparatus for measuring the degree of entanglement in a multifilament yarn according to the present invention comprises:

a feed roll connected to a drive means for normal and reverse rotation, the feed roll feeding the yarn to a measuring zone of degree of entanglement;

a pulley provided in the measuring zone of degree of entangelement, the yarn sent from the feed roll being threaded on the pulley, the pulley being connected to a rotation meter detecting the amount of rotation of the pulley, the pulley being supported free to rotate;

a yarn-forwarding roll connected to a drive means for rotation, the yarn-forwarding roll forwarding the yarn out of the measuring zone of degree of entangelement;

a first tension roll hung movably in a vertical direction by the yarn threaded from the feed roll through the pulley, a weight being attached to the first tension roll;

a second tension roll hung movably in a vertical direction by the yarn threaded from the pulley through the yarn-forwarding roll, an another weight being attached to the second tension roll;

a needle disposed in a position against a yarn path of the yarn positioned between the pulley and either one of the first tension roll and the second tension roll, the needle being capable of advancing and retracting in the direction of the yarn path and capable of piercing the yarn positioned in the yarn path by the advancing;

a first means for adding an auxiliary weight to the first tension roll;

a second means for adding an auxiliary weight to the second tension roll;

a first means for detecting the position of the first tension roll, this first position detecting means being electrically connected to the drive means for normal and reverse rotation;

a second means for detecting the position of the second tension roll, this second position detecting means being electrically connected to the drive means for roration.

In the above apparatus, a multifilament yarn given entanglement is fed into the measuring zone of degree of entanglement, and threaded from the feed roll through the first tension roll, the pulley, the second tension roll and the yarn-forwarding roll in order. The first tension roll and the second tension roll normally have weights of identical value, and the feeding of the yarn is stopped under the state that the first tension roll and the second tension roll are balanced at both sides of the pulley.

Next, the needle pierces the yarn. Then the auxiliary weight is added to one of the first and the second tension rolls, whereby the balance of weight is lost, the yarn positioned round the tension roll given the auxiliary weight moves down, and the pulley rotates. At this time, to prevent the descent of the tension roll more than a specified distance, the position of the tension roll is detected by the position detecting means, the drive means for normal and reverse rotation or the drive means for rotation operates in accordance with the signal from the detecting means, and thereby the feed roll or the yarn-forwarding roll rotates. The yarn begins moving in upward or downward direction, and when the point of entanglement of the yarn reaches the position of the needle, the point of entanglement engages with the needle and thereby the movement of the yarn is stopped. Since the quantity of the movement of the yarn corresponds to the amount of rotation of the pulley, it is easily determined by the rotation meter.

Next, the auxiliary weight is removed from the above tension roll, and an auxiliary weight is similarly added to the another tension roll. Then, the balance of weight between both sides of the pulley is lost, and thereby the yarn moves in the contrary direction to the above direction. Soon, another point of entanglement of the yarn reaches the needle, and when the point of entanglement engages with the needle, the movement of the yarn is stopped. The quantity of the movement of the yarn is also determined easily by the rotation meter connected to the pulley. This quantity of the movement of the yarn corresponds to the distance between mutually adjacent points of entanglement of the yarn, that is, the pitch of points of entanglement (the length of opening). Moreover, since the point of entanglement engages with the needle under the condition wherein the yarn has a definite tension due to adding the auxiliary weight, the data obtained can become one including the strength of entanglement.

By feeding the yarn little by little to the measuring zone of entanglement by the feed roll and by repeating the above series of actions automatically, much data relating to the pitch of points of entanglement can be obtained. The degree of entanglement is obtained by dividing a certain length of the yarn by the above data.

Thus, in the apparatus for measuring the degree of entanglement in a yarn according to the present invention, the degree of entanglement can be automatically determined completely without a high-performance tension meter.

Since the distance of movement of the first and the second tension rolls can be confined within predetermined limits, the measurement of the degree of entanglement due to Hook-drop method can be achieved without enlarging the measuring apparatus, even if the yarn has portions having long pitch of points of entanglement or portions having smaller strength of entanglement than a regular value.

Moreover, since no tension meter is used, data with high accuracy can be obtained.

BRIEF DESCRIPTION OF THE DRAWINGS

The above and other objects, features and advantages of the present invention will become apparent and more readily appreciated from the following detailed description of the preferred exemplary embodiments of the invention, taken in conjunction with the accompanying drawings, in which:

FIG. 17 is a flowchart showing the next step after that shown in FIG. 16;

FIG. 18 is a flowchart showing the next step after that shown in FIG. 17;

FIG. 21 is a schematic side view of an apparatus for measuring the degree of entanglement in a yarn according to another embodiment of the present invention;

DETAILED DESCRIPTION OF THE PREFERRED EMBODIMENTS

Some preferred embodiments of the present invention will be described hereunder referring to the attached drawings.

Figure 1:
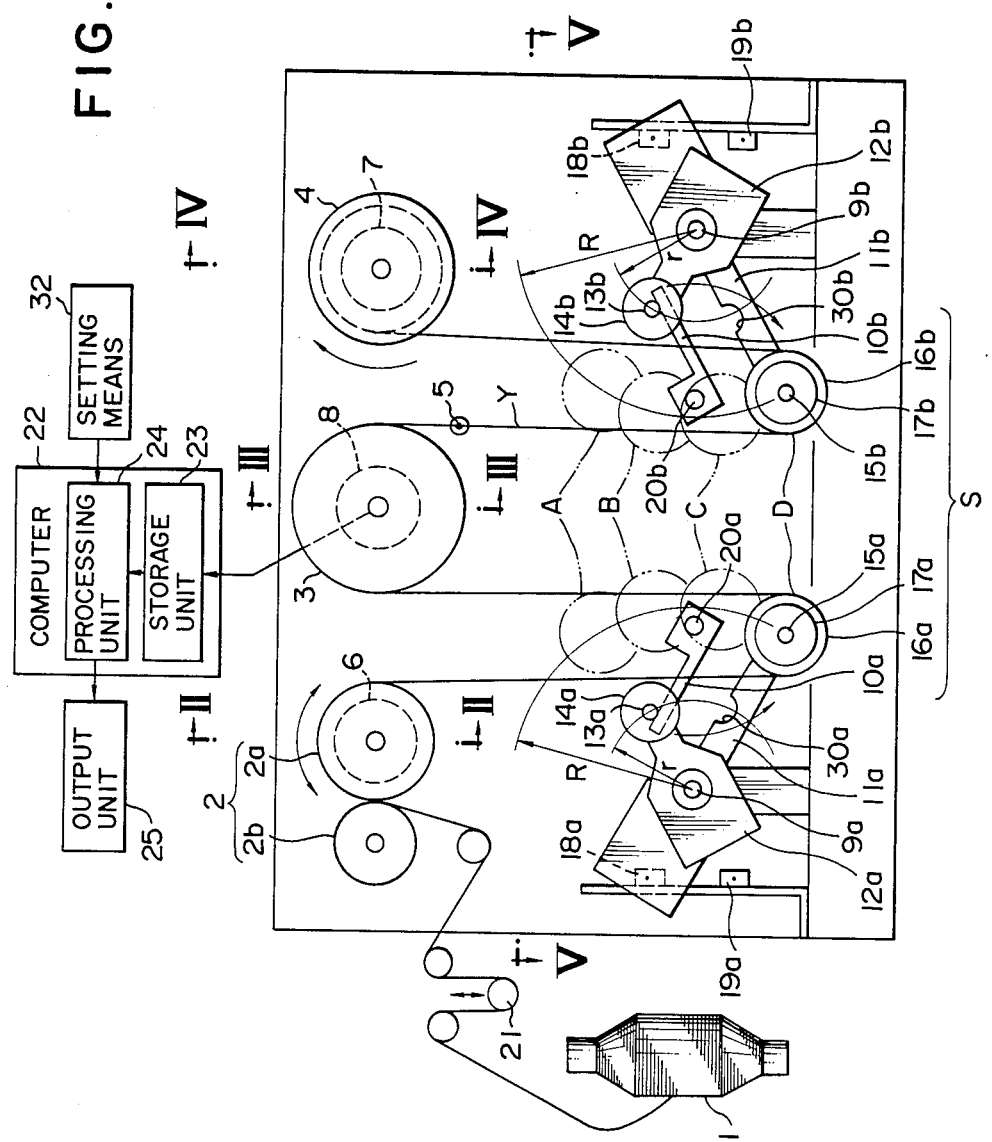
FIG. 1 is a schematic side view of an apparatus for measuring the degree of entanglement in a yarn according to an embodiment of the present invention.

FIG. 1 illustrates an entire constitution of an apparatus for measuring the degree of entanglement in a yarn according to an embodiment of the present invention. Numeral 1 shows a package on which an entangled multifilament yarn Y is wound and the yarn Y becomes a sample for measurement. The multifilament yarn Y is unwound from the package 1 by a feed roll 2 comprising a pair of nip rolls 2a and 2b capable of nipping the yarn Y, and finally the yarn Y is wound round a yarn-winding roll 4. A movable dancer roller 21 as a means for absorbing sag of the yarn Y is provided between the feed roll 2 and the package 1. The zone between the feed roll 2 and the yarn-winding roll 4 is a measuring zone S for measuring the degree of entanglement. The yarn-winding roll 4 constitutes a yarn-forwarding roll for forwarding the yarn Y out of the measuring zone S.

In the measuring zone S between the feed roll 2 and the yarn-winding roll 4, a pulley 3 is provided free to rotate. A first tension roll 16a is provided between the feed roll 2 and the pulley 3. A second tension roll 16b is provided between the pulley 3 and the yarn-winding roll 4.

The multifilament yarn Y sent to the measuring zone S by the feed roll 2 is threaded on the first tension roll 16a, the pulley 3 and the second tension roll 16b in order, and finally wound by the yarn-winding roll 4. The first tension roll 16a is hung by the yarn Y threaded between the feed roll 16a and the pulley 3 so as to permit the movement of the first tension roll 16a in the vertical direction. The second tension roll 16b is hung by the yarn Y threaded between the pulley 3 and the yarn-winding roll 4 so as to permit the movement of the second tension roll 16b in the vertical direction.

Figure 2:
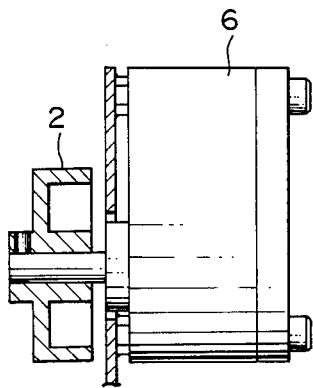
FIG. 2 is an enlarged partial sectional view taken along II—II in FIG. 1, of a feed roll of the apparatus.

As shown in FIG. 2, a drive means comprising a motor 6 for normal and reverse rotation is connected to the feed roll 2, and the drive means for normal and reverse rotation 6 can change the peripheral speed of the feed roll 2 and the direction of rotation of the feed roll 2.

Figure 4:
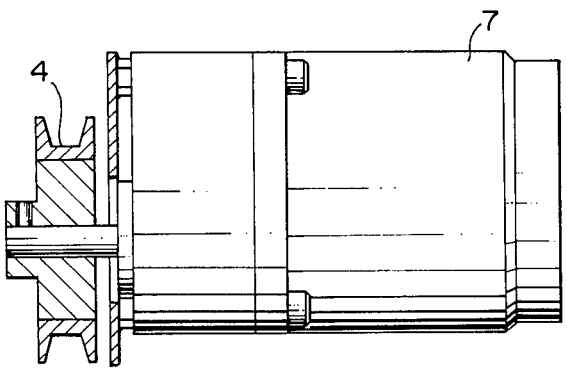
FIG. 4 is an enlarged partial sectional view taken along IV—IV in FIG. 1, of a yarn-forwarding roll of the apparatus.

Similarly, as shown in FIG. 4, a drive means for rotation comprising a motor 7 is connected to the yarn-winding roll 4, and the drive means for rotation 7 can control the peripheral speed of the yarn-winding roll 4. In this embodiment the motor 7 is also capable of reverse rotation.

Figure 3:
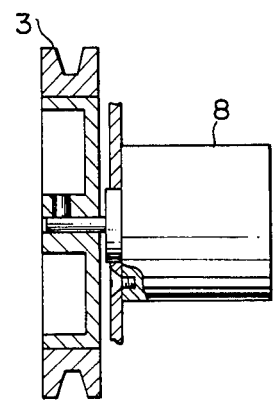
FIG. 3 is an enlarged partial sectional view taken along III—III in FIG. 1, of a pulley of the apparatus.

Moreover, as shown in FIG. 3, a rotary encoder 8 is connected to the pulley 3, and the rotary encoder 8 constitutes a rotation meter detecting the amount of rotation of the pulley 3. The signal from the rotary encoder 8 is sent to a computer 22 (or a micro computer), is memorized in a storage unit 23 of the computer 22, and calculation is performed using the signal in a processing unit 24 of the computer 22, then the result of the calculation is sent to a output unit 25.

A needle 5 is disposed in a position against the yarn path of the yarn Y between the pulley 3 and the second tension roll 16b. The needle 5 is actuated in the direction perpendicular or nearly perpendicular to the yarn path of the yarn Y and is actuated for advancing to the position of piercing the yarn Y and retracting out of the yarn Y by a drive means.

Figure 6:
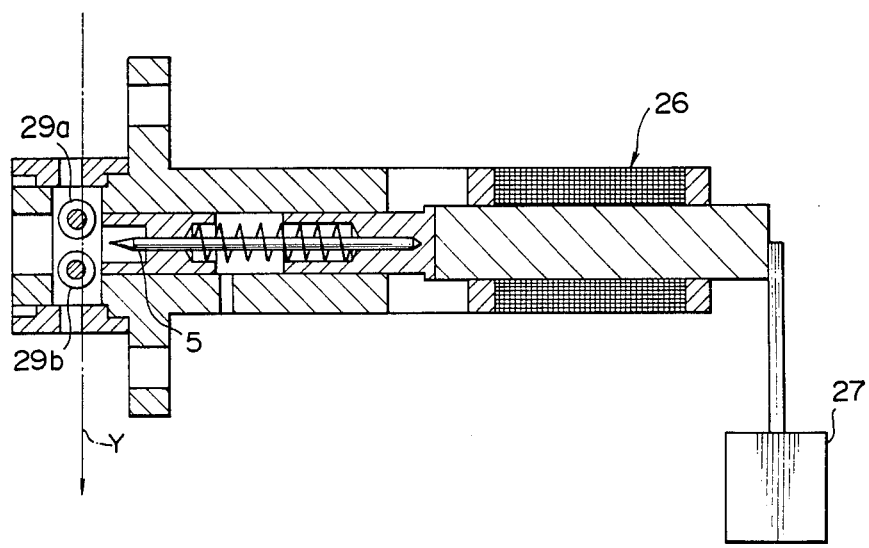
FIG. 6 is an enlarged vertical sectional view of a portion, including a needle shown in FIG. 1, of the apparatus.
Figure 7:
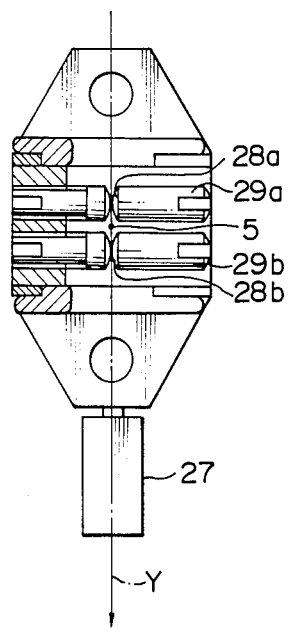
FIG. 7 is a elevational view (partly cut away) shown in FIG. 6.

The drive means for advancing and retracting the needle 5 comprises a solenoid 26, as shown in FIG. 6. When the solenoid 26 is on, the needle 5 retracts the yarn Y, and when the solenoid 26 is off, the needle 5 retracts out of the yarn Y. As a means for detecting the advancing and retracting of the needle 5, a limit switch 27 is provided. Guide pins 29a and 29b with grooves 28a and 28b guiding the yarn Y are provided at both sides of the position where the needle 5 pierces the yarn Y. The yarn path of the yarn Y is regulated to a predetermined yarn path by the guide pins 29a and 29b.

Tension rolls 16a and 16b are supported free to rotate on shafts 15a and 15b respectively. The shafts 15a and 15b are fixed to tip portions of arms 11a and 11b swingably pivoted on shafts 9a and 9b respectively. To the shafts 15a and 15b, weights 17a and 17b are also attached respectively. The weights 17a and 17b can be easily attached and removed against the shafts 15a and 15b, and the weight thereof can be changed appropriately.

The shafts 9a and 9b support auxiliary arms 12a and 12b (swing arms) free to swing besides the arms 11a and 11b. Pins 13a and 13b are fixed to the tip portions of auxiliary arms 12a and 12b respectively. Auxiliary weights 14a and 14b are attached to the pins 13a and 13b respectively. The auxiliary weights 14a and 14b can be also easily attached and removed against the pins 13a and 13b, and the weight thereof can be changed appropriately.

Figure 5:
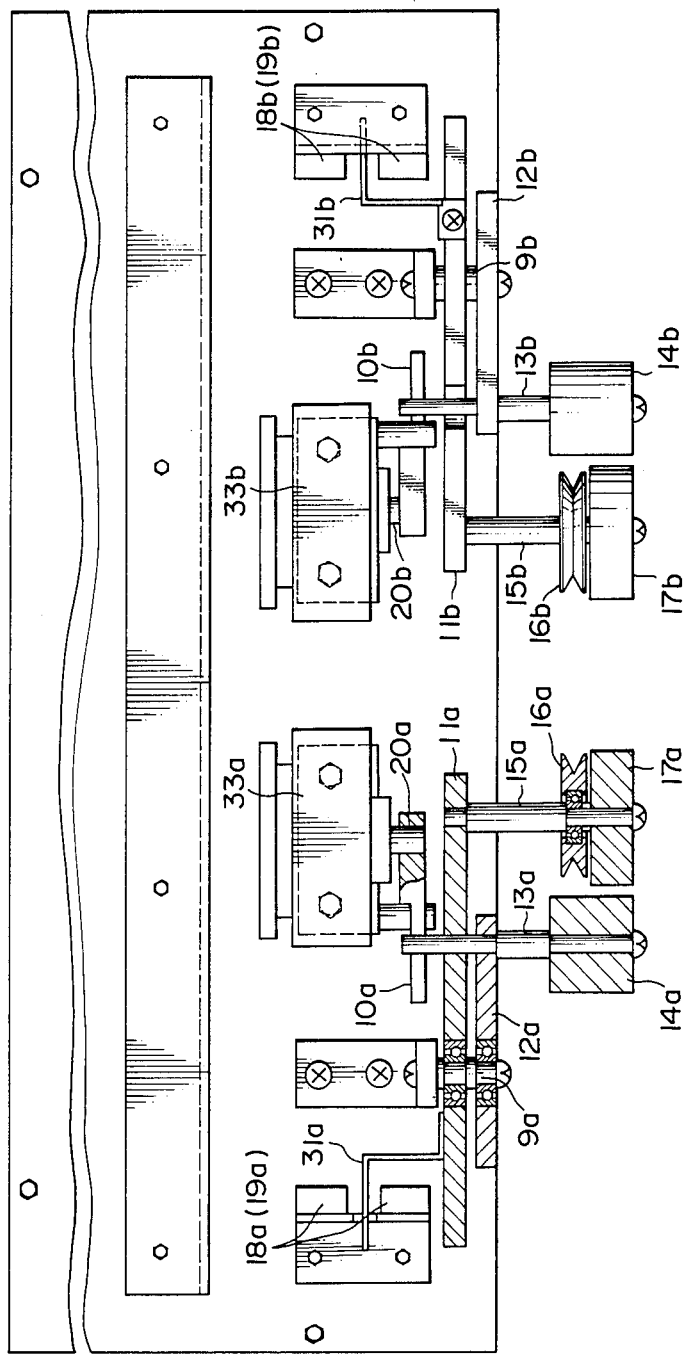
FIG. 5 is a plan view taken along V—V in FIG. 1, partly in section.

In position against the auxiliary arms 12a and 12b are provided stoppers 10a and 10b, and the stoppers 10a and 10b can be swung round fulcrums 20a and 20b by drive units 33a and 33b (FIG. 5). The stoppers 10a and 10b are constituted so as to be able to support the pins 13a and 13b at the tip portions of the stoppers 10a and 10b, thus also supporting the auxiliary weights 14a and 14b on the pins 13a and 13b. The pins 13a and 13b can be inserted into recess portions 30a and 30b formed in the upper surfaces of the arms 11a and 11b. When the pins 13a and 13b are released from the stoppers 10a and 10b, the auxiliary arms 12a and 12b are swung downward and the pins 13a and 13b are supported on the recess portions 30a and 30b, and the weights of the auxiliary weights 14a and 14b are added to the arms 11a and 11b respectively. Therefore, in this state the weight due to the auxiliary weights 14a and 14b besides the weight due to the weights 17a and 17b is added to the tension rolls 16a and 16b.

When measuring the degree of entanglement in the multifilament yarn Y, the yarn Y is threaded between the feed roll 2 and the pulley 3 so as to hang the first tension roll 16a and threaded between the pulley 3 and the yarn-winding roll 4 so as to hang the second tension roll 16b. Accordingly, when the length of the yarn Y threaded between the feed roll 2 and the yarn-winding roll 4 changes, the first and the second tension rolls 16a and 16b move in the vertical direction.

Moreover, when there occurs a difference between the forces working on the arms 11a and 11b supporting the first and the second tension rolls 16a and 16b, the tension rolls 16a and 16b and the arms 11a and 11b move mutually in opposite directions.

As means for detecting the positions of the first and the second tension rolls 16a and 16b, a first position detecting means and a second position detecting means are provided respectively. The first position detecting means comprises photoelectric switches 18a and 19a detecting the position of arm 11a, and the second position detecting means comprises photoelectric switches 18b and 19b detecting the position of arm 11b. The photoelectric switches 18a and 19a are provided behind the arm 11a, and the photoelectric switches 18b and 19b are provided behind the arm 11b. As shown in FIG. 5, each photoelectric switch detects the positions of arms 11a and 11b respectively via a detecting plate 31a fixed to the arm 11a and a detecting plate 31b fixed to the arm 11b. The photoelectric switches 18a and 18b detect the positions of arms 11a and 11b and issue detecting signals, when the tension rolls 16a and 16b are in the range between a position C and a position D shown in FIG. 1. The photoelectric switches 19a and 19b detect the positions of arms 11a and 11b and issue detecting signals, when the tension rolls 16a and 16b are in the range between a position A and a position B shown in FIG. 1.

The auxiliary arms 12a and 12b are balanced so that the angular moments around shafts 9a and 9b become zero when auxiliary weights 14a and 14b are removed from the auxiliary arms 12a and 12b. Similarly, the arms 11a and 11b are balanced so that the angular moments around shafts 9a and 9b become zero when weights 17a and 17b are removed from the arms 11a and 11b.

The weights 17a and 17b are identical in weight, and the auxiliary weights 14a and 14b are also identical in weight. The weight $W_1$ of the weights 17a and 17b and the weight $W_2$ of the auxiliary weights 14a and 14b are determined, for instance, in accordance with the total denier D and the number of filaments of the multifilament yarn Y. An example of the manner for determining the weights $W_1$ and $W_2$ is shown as follows.

$$T_1 = D/10 \tag{1}$$

$$T_2 = 2 \times D/F \tag{2}$$

$$W_1 = 2 \times T_1 \tag{3}$$

$$W_2 = 2 \times T_2 \times (R/r) \tag{4}$$

D; total denier,
F; the number of filaments,
$T_1$; pretension always added during the measurement,
$T_2$; tripping tension added to the pretension,
R; the radius of gyration of a tension roll,
r; the radius of gyration of the pins 13a, 13b round shafts 9a, 9b respectively,
$W_1$; the weight of a weight, and
$W_2$; the weight of an auxiliary weight.

As shown clearly in the above formulas, the weight $W_1$ of the weights 17a and 17b and the weight $W_2$ of the auxiliary weights 14a and 14b have different values depending on kinds of multifilament yarns Y. Therefore, number of different weights 17a and 17b and auxiliary weights 14a and 14b are prepared, so that the appripriate weights can be applied depending on the measuring yarn Y.

Next, the measurement of the degree of entanglement using the above measuring apparatus is described.

First, different the weights 17a and 17b and the auxiliary weights 14a and 14b corresponding to the multifilament yarn Y to be measured are attached to shafts 15a and 15b and pins 13a and 13b. Then the multifilament yarn Y unwound from the package 1 is threaded on the feed roll 2, the first tension roll 16a, the pulley 3 and the second tension roll 16b in order, and finally wound round the yarn-winding roll 4.

Figure 20:
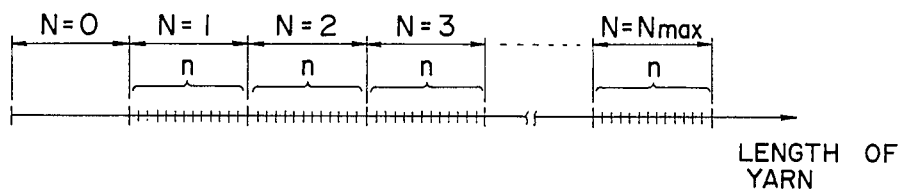
FIG. 20 is a graph showing a relationship between the pitch of feeding the yarn and the times of piercing of the needle in the operation of the apparatus in FIG. 1.

Then the length N of samples of the yarn Y which should be sent to the measuring zone S in turn and the number n of times that the needle 5 should pierce the yarn Y within the length N of the sample are set by a setting means 32 connected to the processing unit 24 of the computer 22. As shown in FIG. 20, it is desirable to set a plurality of the lengths N of the sample in the feeding direction of the yarn. In the case of setting a plurality of the lengths N, the number n of times of piercing of the needle 5 is set upon each sample length N. The value of N and n can be changed appropriately.

Figure 11:
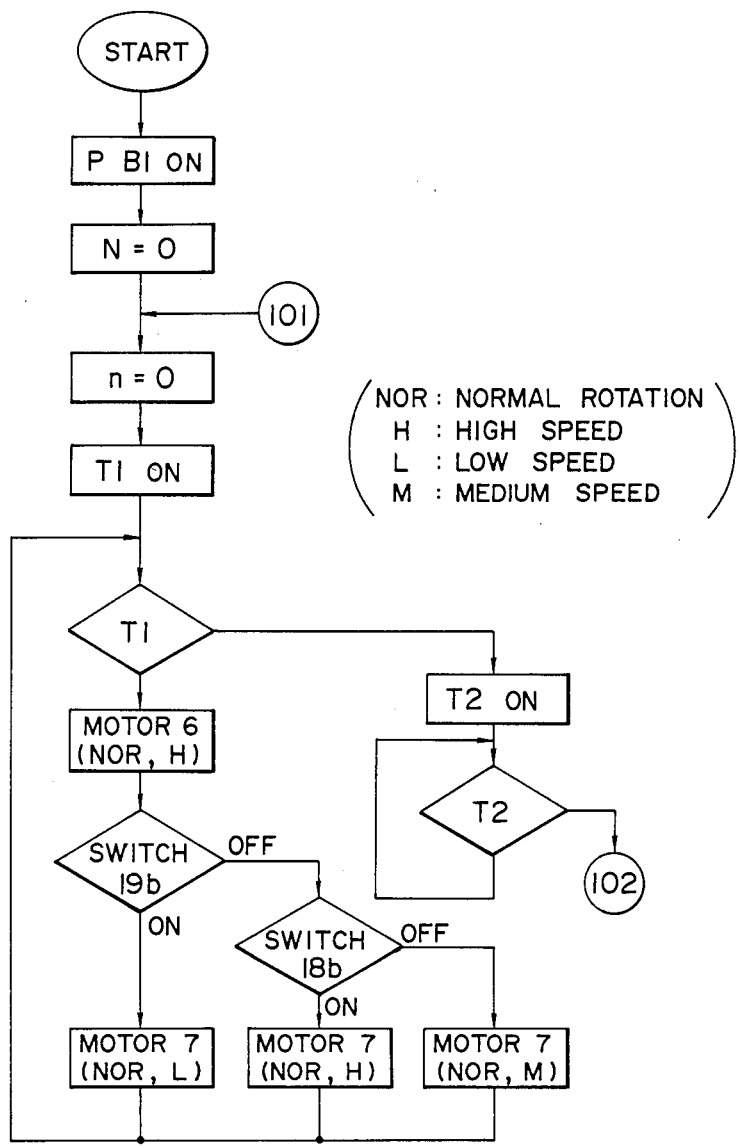
FIG. 11 is a flowchart of a computer shown in FIG. 1 illustrating a step in the operation.

Next, the first step 101 in the processing unit 24 is shown in FIG. 11. When a starting switch PB1 for the measurement is closed, N is counted as zero, and then the motor 6 rotates in the normal direction during a certain time (for example, 10 seconds) set on timer T1, whereby the feed roll 2 feeds the yarn Y at a predetermined high speed. The fed yarn Y is wound to the yarn-winding roll 4 so as to secure the positions of the first and the second tension rolls 16a and 16b within the predetermined range. Since the first tension roll 16a and the second tension roll 16b are balanced on weight on both sides of pulley 3, the above control of the first and the second tension rolls 16a and 16b is achieved sufficiently by only controlling the speed of the yarn-winding roll 4 in accordance with the position of the second tension roll 16b. Namely, if the photoelectric switch 19b is on, this indicates that the winding of the yarn Y is faster than the feeding, and therefore the speed of the motor 7 for the yarn-winding roll 4 is controlled to a low speed. If the photoelectric switch 19b is off and the photoelectric switch 18b is on, this indicates that the winding of the yarn Y is slower than the feeding, and therefore the speed of the motor 7 is controlled to a high speed. If both of photoelectric switches 18b and 19b are off, the feeding and winding of the yarn Y are balanced, and therefore the speed of the motor 7 is controlled to a medium speed. Thus, the yarn Y with a predetermined length is stripped from the surface portion of the package 1. In this action, the tension of the yarn Y in the measuring zone S is determined by the weights added to the tension rolls 16a and 16b, and the tension is kept constant. Before proceeding to the next step, a certain time set on a timer T2 is given to prevent the entering of error signals.

Figure 12:
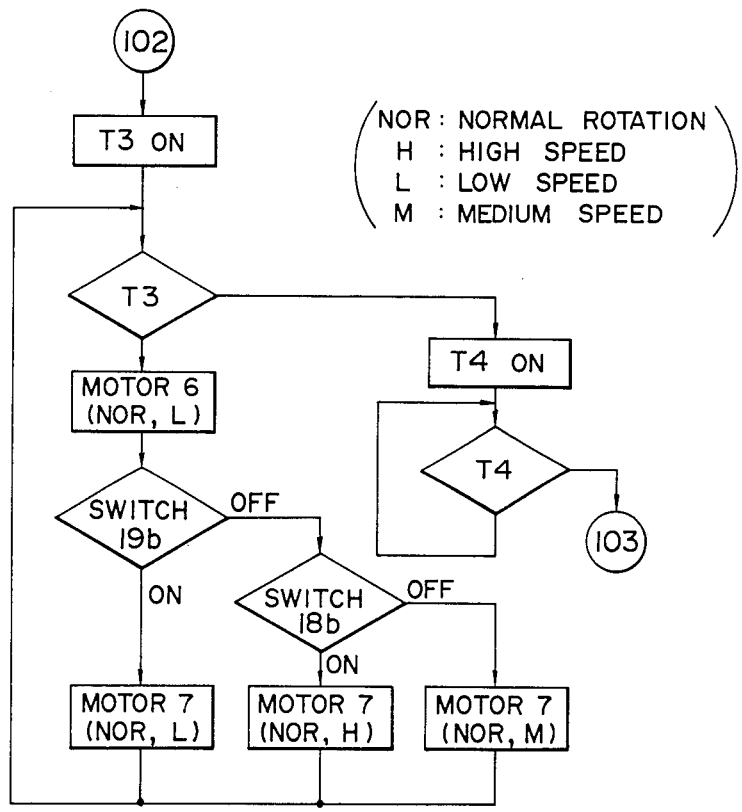
FIG. 12 is a similar flowchart showing the next step in the operation.

Next, the second step 102 is shown in FIG. 12. The speed of the motor 6 is changed to a low speed for a certain short time set on a timer T3, and a measuring point of the yarn Y is settled by the same control of the positions of tension rolls 16a and 16b as the control in step 101. The running of the yarn Y is stopped after the settlement of the measuring point. Before proceeding to the next step, a certain time is given by a timer T4.

Figure 13:
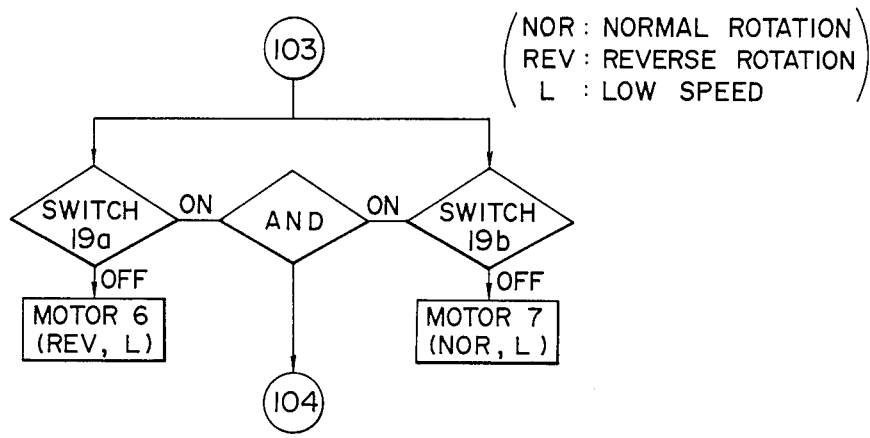
FIG. 13 is a flowchart showing the next step after that shown in FIG. 12.

Next, the first and the second tension rolls 16a and 16b are moved toward the upper limit positions. As the third step 103 shown in FIG. 13, the feed roll 2 and the yarn-winding roll 4 rotate in normal or reverse direction depending on the signals from the photoelectric switches 19a and 19b, and thereby the first and the second tension rolls 16a and 16b are moved to the position B in FIG. 1.

The detecting plates 31a and 31b are constituted so that the photoelectric switches 19a and 19b can be always on when the tension rolls 16a and 16b are positioned above than the position A.

Figure 9:
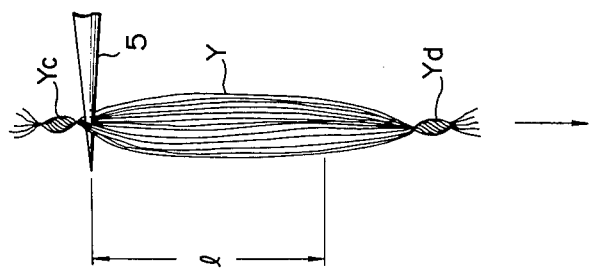
FIG. 9 is an enlarged side view of the needle and the yarn, showing a next state from that shown in FIG. 8.
Figure 8:
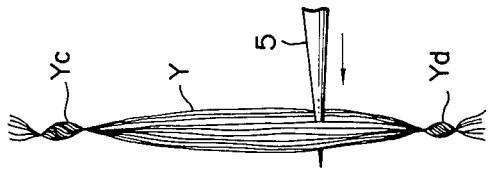
FIG. 8 is an enlarged side view of the needle and yarn in FIG. 1, showing a state wherein the yarn is pierced by the needle.
Figure 14:
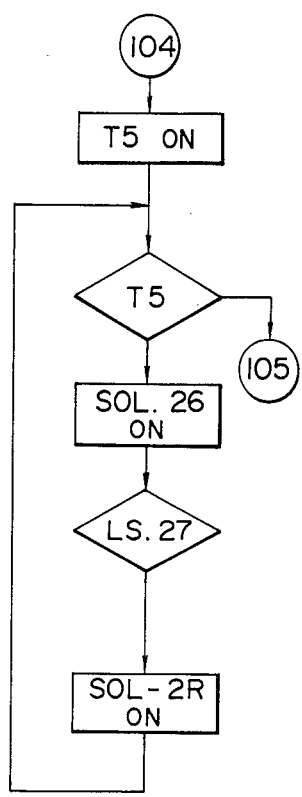
FIG. 14 is a flowchart showing the next step after that shown in FIG. 13.

Next, the fourth step 104 is shown in FIG. 14. After a certain time is given by a timer T5, the solenoid 26 becomes on and thereby the needle 5 is projected. This action is confirmed by the limit switch 27. When the needle 5 advances, the needle 5 pierces the yarn Y as shown in FIG. 8. This position where the needle 5 has pierced the yarn Y is memorized in the storage unit 23 according to the signal from the limit switch 27, and memorized as a signal of a starting point for measurement of the movement distance l shown in FIG. 9. When the needle 5 has pierced the yarn Y, a solenoid SOL-2R for the drive unit 33b works, the stopper 10b is actuated by the drive unit 33b, and the auxiliary weight 14b is imposed on the arm 11b via the pin 13b. As a result, weight $W_2 \times (r/R)$ due to the auxiliary weight 14b beside the weight due to the weight 17b is added to the second tension roll 16b, and there occurs a weight difference between the first tension roll 16a and the second tension roll 16b. On account of the weight difference, the second tension roll 16b moves down, and at the same time the yarn Y moves down, thus moving down an upper point of entanglement Yc, as shown in FIG. 9. Then the multifilament yarn Y stops after moving down a distance l such that the upper point of entanglement Yc reaches the needle 5.

Figure 15:
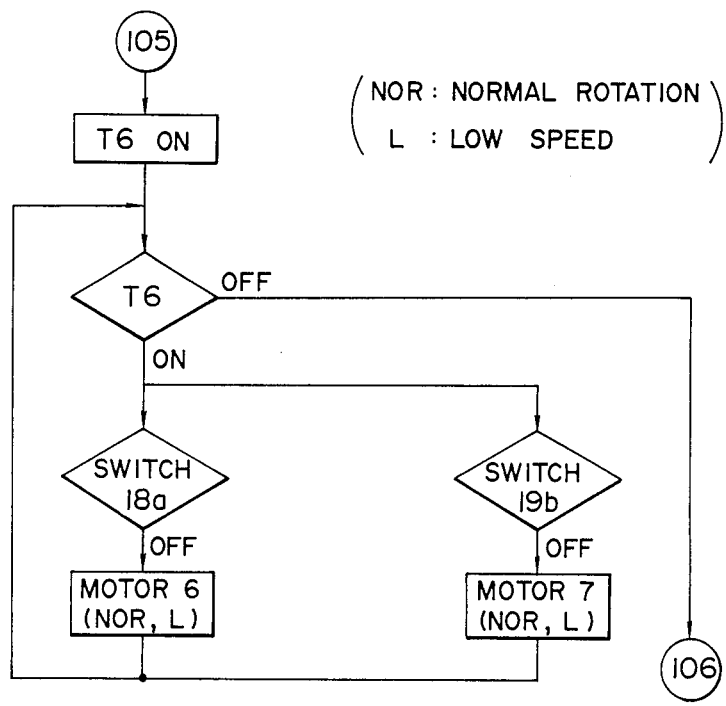
FIG. 15 is a flowchart showing the next step after that shown in FIG. 14.

In the measurement, a timer T6 starts almost at the same time as the timer T5 started, as the fifth step 105 shown in FIG. 15. The next action begins after about 2 seconds from the time at that the timer T6 becomes on, even in the case where the needle 5 misses and fails to pierce the yarn Y.

When the distance l is large or when the strength of the point of entanglement Yc is smaller than the value determined from aforementioned formulas (2) and (4), the arm 11b is liable to swing down to a considerable extent. However, since the motor 7 for the yarn-winding roll 4 operates in response to the detecting signal of the photoelectric switch 18b when the arm 11b reaches the position C and thereby the yarn Y is wound by the yarn-winding roll 4, the yarn Y is fed without undue downward movement of the arm 11b. This winding is continued till the arm 11b returns to the position B after the engagement of the point of entanglement Yc or a further upper point of entanglement Yc with the needle 5. When the arm 11b reaches the position B, the drive motor 7 stops in accordance with the detecting signal of the photoelectric switch 19b, and the winding of the yarn-winding roll 4 is stopped. The detecting signal is sent to the computer 22 and memorized as a signal of an ending point for measurement of the movement distance l and as a signal of a starting point for measurement of the movement distance L shown in FIG. 10.

The movement distance l of the point of entanglement Yc is measured by detecting the amount of rotation of the pulley 3, and the detected signal is sent to the computer 22 from the rotary encoder 8 and memorized. Moreover, in the measurement, if the photoelectric switch 18a is off, the motor 6 rotates in normal direction at a low speed, as shown in FIG. 15, and thereby the yarn Y is fed. This is because the first tension roll 16a is raised in the upper position, so it is necessary to feed more of the yarn Y. If the photoelectric switch 19b is off, the motor 7 rotates in normal direction at a low speed. This is because the second tension roll 16b has moved down to the lower position and the point of entanglement Yc does not reach the needle 5, so it is necessary to forward more of the yarn Y.

Next, the sixth step 106 is shown in FIG. 16. After a certain time set on a timer T7 has elapsed, the motor 7 rotates in reverse direction at a low speed if the photoelectric switch 18b is off. The second tension roll 16b is moved down by the above operation and according to the movement of the second tension roll 16b the first tension roll 16a is moved up, and thereby occurrence of a shock can be prevented when the next changes of auxiliary weight occur.

Figure 10:
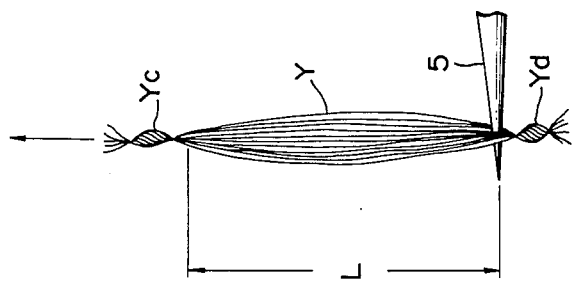
FIG. 10 is an enlarged side view of the needle and the yarn, showing a next state from that shown in FIG. 9.

Next, the seventh step 107 is shown in FIG. 17. The solenoid SOL-2R for the drive unit 33b driving the stopper 10b becomes off, and the stopper 10b is returned to the former position. The auxiliary weight 14b is also returned to the former position accompanying the returning of the stopper 10b. Then, a solenoid SOL-2L for the drive unit 33a driving the stopper 10a becomes on, and the stopper 10a is swung down. Accompanying this swinging down of the stopper 10a, the auxiliary weight 14a is also moved down, and thereby the auxiliary weight 14a is imposed on the arm 11a via the pin 13a. As a result, weight $W_2 \times (r/R)$ due to the auxiliary weight 14a beside the weight due to the weight 17a is added to the first tension roll 16a, and there occurs a weight difference between the first tension roll 16a and the second tension roll 16b. On account of the weight difference, the first tension roll 16a moves down, at the same time the yarn Y moves up together with moving up of a lower point of entanglement Yd as shown in FIG. 10, and the yarn Y stops after moving up by the distance L, indicating that the lower point of entanglement Yd has reached the needle 5.

In the measurement, if the above movement of the yarn Y is not stopped within a predetermined short time set by a timer T9, the following action is performed, as the eighth step 108 shown in FIG. 18. Namely, when the movement distance L is large or when the strength of the point of entanglement Yd is smaller than the value determined from aforementioned formulas (2) and (4), the arm 11a is liable to swing down to a considerable extent. However, the drive motor 6 for the feed roll 2 rotates in reverse direction in response to the detecting signal of the photoelectric switch 18a when the arm 11a reaches the position C, and thereby the yarn Y is wound back in the direction of the package 1 by the feed roll 2. This winding back is continued till the arm 11a returns to the position B after the engagement of the point of entanglement Yd or a further lower point of entanglement Yd to the needle 5. When the arm 11a reaches the position B, the winding back due to the feed roll 2 is stopped in accordance with the detecting signal of the photoelectric switch 19a. The detecting signal is sent to the computer 22 and memorized as a signal of a ending point for measurement of the movement distance L.

The movement distance L of the point of entanglement Yd in the multifilament yarn Y is measured by detecting the amount of rotation of the pulley 3, and the detected signal is sent to the computer 22 from the rotary encoder 8 and memorized. Moreover, in the measurement, if the photoelectric switch 19a is off, the motor 6 rotates in reverse direction at a low speed, as shown in FIG. 18. When the point of entanglement Yd is engaged with the needle 5, the first tension roll 16a is moved up by the winding back of the yarn Y due to the reverse rotation of the motor 6, and the photoelectric switch 19a becomes on. If the photoelectric switch 18b is off, the motor 7 rotates in reverse direction at a low speed, and thereby the yarn Y necessary to the movement of the point of entanglement of the yarn Yd is unwound. Since the movement of the yarn Y is stopped when the point of entanglement Yd engages with the needle 5, the second tension roll 16b is moved down by the unwinding of the yarn Y due to the reverse rotation of the motor 7, and the photoelectric switch 18b becomes on. The distance L is measured as described above.

Figure 19:
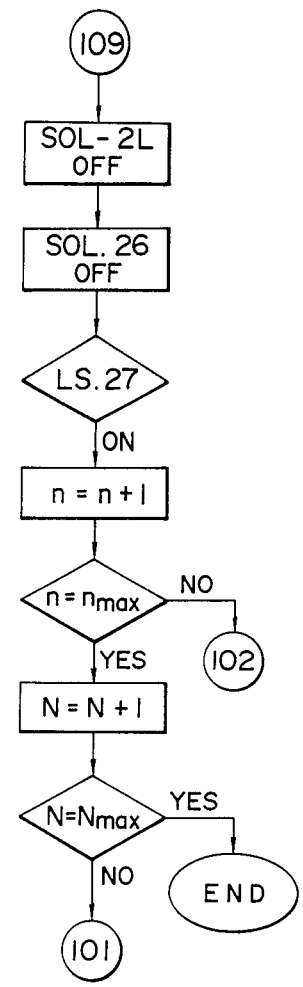
FIG. 19 is a flowchart showing the next step after that shown in FIG. 18.

Next, the ninth step 109 is shown in FIG. 19. The solenoid SOL-2L becomes off, the stopper 10a is returned to the former position, and the auxiliary weight 14a is removed from the arm 11a. Then the solenoid 26 switches off and thereby the needle 5 is retracted from the piercing position to the yarn Y. This action is confirmed by the limit switch 27 and then next loop begins.

Then, the above operation is repeated n times according to requirements, and obtained data of L and l in the measurement are memorized in the storage unit 23 of the computer 22. In the above measurement, the needle 5 pierces the yarn Y n times within the length of a sample (a zone of the yarn Y fed from the package 1), and the needle 5 also pierces the yarn Y n times in the next sample. These datas of L and l are calculated to average data Lav (cm) lav (cm) respectively in the processing unit 24. Also, the degrees of entanglement 100/Lav and 100/lav are calculated, and they are put out from the output unit 25. Both the degree of entanglement on the basis of the data L and the degree of entanglement on the basis of the data l indicate the degree of entanglement in the yarn Y. However, since a result on the basis of the data L indicates the degree of entanglement based on accurate measurement of the length of opening between the points of entanglement, the degree of entanglement on the basis of the data L can indicate the strength of entanglement in a multifilament yarn more accurately in comparison with one on the basis of the data l.

In the measurement shown in FIG. 20, N and n can be changed. If the weight of the weights 17a and 17b or the auxiliary weights 14a and 14b is changed at a zone N chosen appropriately, a formula can be derived for a paramenter K, indicating any change in the degrees of entanglement, as measured under different conditions. In the aforementioned operations the points of entanglement Yc and Yd, and the length of opening and degree of entranglement are measured under the condition wherein a predetermined tension is given to the yarn Y by the weights 17a and 17b and the auxiliary weight 14a or 14b. Therefore, by measuring the degree of entanglement CFa under a tension of the yarn Y and the degree of entanglement CFb under another tension of the yarn Y due to changing the weights, and by comparing them in the processing unit 24, the paramenter K can be obtained, calculated, for example, as follows:

$$K = CFb/CFa \quad (5)$$

or $$K = (CFa - CFb)/CFb \quad (6)$$

or $$K = (CFa - CFb)/CFa \quad (7)$$

This parameter K indicates a rate for keeping the strength of entanglement in the yarn Y.

Next, an another embodiment of the present invention is shown in FIG. 21. Numeral 41 shows a feed roll, numeral 42 shows a pulley and numeral 43 shows a yarn-forwarding roll. The yarn-forwarding roll 43 comprises a pair of nip rolls 43a and 43b, and can draw-out and feed the yarn Y to a next process without winding the yarn Y. Numeral 44a shows a first tension roll and numeral 44b shows a second tension roll. In this embodiment, the first and the second tension rolls 44a and 44b are provided free to rotate at tip portions of arms 46a and 46b capable of swinging round fulcrums 45a and 45b. To the tension rolls 44a and 44b, weights (not shown) are attached.

In the measurement of the degree of entanglement, a needle 47 pierces the yarn Y threaded from the pulley 42 to the yarn-forwarding roll 43 through the second tension roll 44b. The positions of the arms 46a and 46b, that is, the positions of the tension rolls 44a and 44b are detected by the photoelectric switches 48a and 49a and the photoelectric switches 48b and 49b.

Auxiliary weights 51a and 51b, supported by auxiliary arms 50a and 50b, are provided under the arms 46a and 46b. The auxiliary weights 51a and 51b are connected to the arms 46a and 46b by means 52a and 52b capable of suspending the auxiliary weights 51a and 51b, for example, wires. When the auxiliary arms 50a and 50b are swung down, the auxiliary weights 51a and 51b are suspended from the arms 46a and 46b by the suspending means 52a and 52b, and the weights of the auxiliary weights 51a and 51b are added to the first and the second tension rolls 44a and 44b respectively.

Also in this apparatus, the movement distance l of the yarn Y from the position where the needle 47 pierces the yarn Y to the position where the point of entanglement is engaged with the needle 47, is measured by detecting the amount of rotation of the pulley 42. The distance L between mutually adjacent points of entanglement is also measured by detecting the amount of rotation of the pulley 42. The distances l and L are detected by a rotary encoder (not shown), and the detected signals are sent to a computer (not shown).

The operation and calculation in the measurement are performed similarly as in the aforementioned embodiment.

In the above two embodiments, although the nip rolls 2a and 2b or 41a and 41b are applied as the feed roll 2 or 41, a non-nip type feed roll can be applied as long as the yarn Y does not slip on a feed roll. Moreover, as regards the position where the needle 5 or 47 is provided, a position between the first tension roll 16a or 44a and the pulley 3 or 42 may be chosen instead of a position between the pulley 3 or 42 and the second tension roll 16b or 44b.

Figure 22:
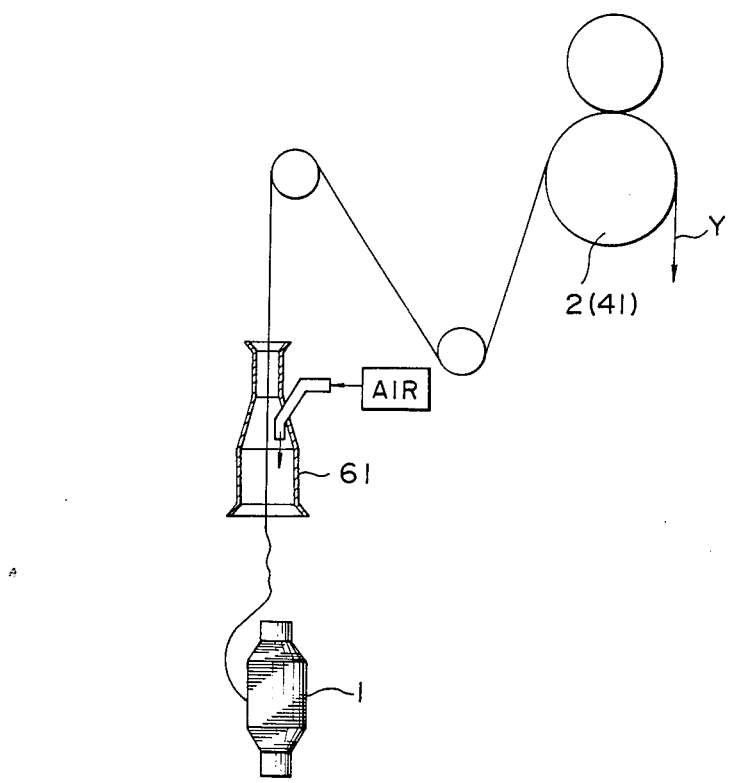
FIG. 22 is a schematic partial side view of an apparatus for measuring the degree of entanglement in a yarn according to a further embodiment of the present invention.
Figure 23:
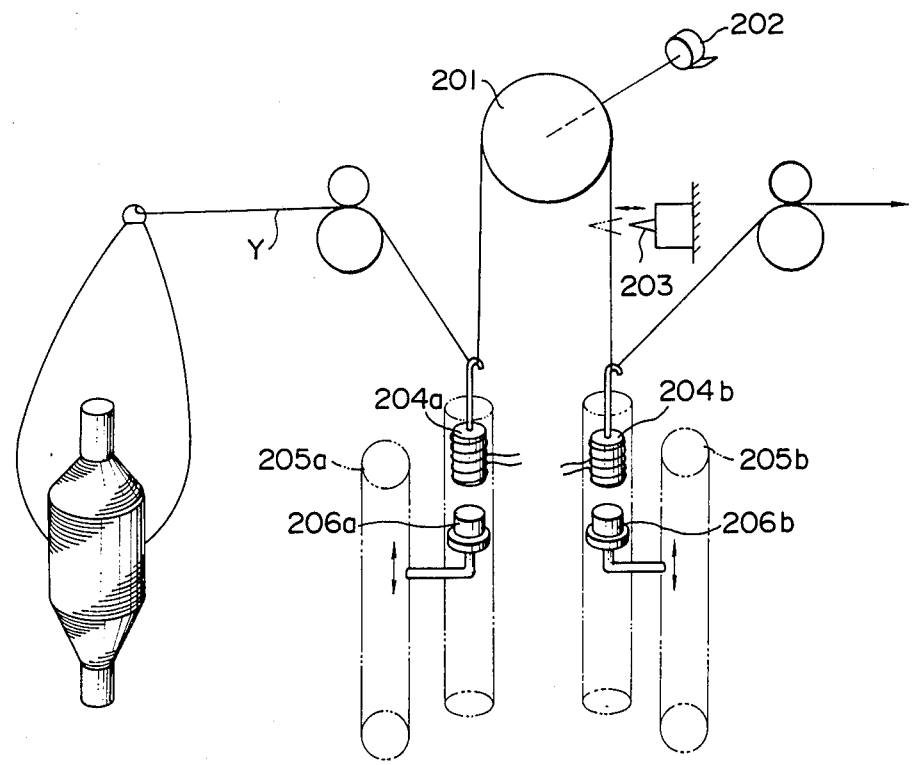
FIG. 23 is a schematic side view of an apparatus for measuring the degree of entanglement in a yarn according to the Prior Art (disclosed in JP-A No. 58-115170).

As regards the means for absorbing sag of the yarn, provided upstream the feed roll 2 or 41, this may be performed by an air ejector 61 as shown in FIG. 22, in place of the means shown in FIG. 1.

Although only several preferred embodiments of the present invention have been described in detail, it will be appreciated by those skilled in the art that various modifications and alterations can be made to the particular embodiments shown without materially departing from the novel teachings and advantages of this invention. Accordingly, it is to be understood that all such modifications and alterations are included within the scope of the invention as defined by the following claims.

What is claimed is:

1. An apparatus for measuring the degree of entanglement in a multifilament yarn comprising:
   a feed roll connected to a drive means for normal and reverse rotation, the feed roll feeding the yarn to a measuring zone of degree of entanglement;
   a pulley provided in the measuring zone of degree of entanglement, the yarn sent from the feed roll being threaded on the pulley, said pulley being connected to a rotation meter detecting the amount of rotation of said pulley, said pulley being supported free to rotate;
   a yarn-forwarding roll connected to a drive means for rotation, the yarn-forwarding roll forwarding the yarn out of the measuring zone of degree of entanglement;
   a first tension roll hung movably in a vertical direction by the yarn threaded from the feed roll through the pulley, a weight being attached to the first tension roll;
   a second tension roll hung movably in a vertical direction by the yarn threaded from the pulley through the yarn-forwarding roll, another weight being attached to the second tension roll;
   a needle disposed in a position against a yarn path of the yarn positioned between the pulley and either one of the first tension roll and the second tension roll, the needle being capable of advancing and retracting in the direction of the path of the yarn and capable of piercing the yarn positioned in said yarn path by said advancing;
   a first means for adding an auxiliary weight to the first tension roll;
   a second means for adding an auxiliary weight to the second tension roll;
   a first means for detecting the position of the first tension roll, this first position detecting means being electrically connected to said drive means for normal and reverse rotation;
   a second means for detecting the position of the second tension roll, this second position detecting means being electrically connected to said drive means for rotation.

2. The apparatus of claim 1, wherein a means for absorbing sag of the yarn is provided upstream of the feed roll.

3. The apparatus of claim 2, wherein the means for absorbing sag of the yarn is an air ejector.

4. The apparatus of claim 2, wherein means for absorbing sag of the yarn is a dancer roller.

5. The apparatus of claim 1, wherein the feed roll comprises a pair of nip rolls capable of nipping the yarn.

6. The apparatus of claim 1, wherein the rotation meter is connected to a computer having a storage unit and a processing unit.

7. The appratus of claim 1, wherein said drive means for rotation comprises a drive means having normal and reverse rotation.

8. The apparatus of claim 1, wherein at least one of said first means for adding an auxiliary weight and said second means for adding an auxiliary weight comprises a means having a swing arm with an auxiliary weight.

9. The apparatus of claim 1, wherein at least one of said first means for adding an auxiliary weight and said second means for adding an auxiliary weight comprises a means capable of suspending an auxiliary weight.

10. The apparatus of claim 1, wherein the yarn-forwarding roll comprises a yarn-winding roll winding the yarn.

11. The apparatus of claim 1, wherein the yarn-forwarding roll comprises a drawing-out roll leading the yarn out of the measuring zone of degree of entanglement.

12. The apparatus of claim 1, wherein the direction of advancing and retracting of the needle is a direction perpendicular or nearly perpendicular to the path of the yarn.

13. The apparatus of claim 1, wherein the needle is connected to a drive means for advancing and retracting the needle.

14. The apparatus of claim 13, wherein said drive means is a solenoid.

15. The apparatus of claim 1, wherein a means for detecting the advancing and retracting of the needle is provided in the position where the needle is provided.

16. The apparatus of claim 1, wherein the movement of the yarn is regulated by guides at both sides of the position where the needle pierces the yarn.

17. The apparatus of claim 1, wherein said first position detecting means and said second position detecting means are noncontact type position detecting means.

18. The apparatus of claim 17, wherein said noncontact type position detecting means is a photoelectric switch.

19. The apparatus of claim 1, wherein said apparatus for measuring the degree of entanglement has a setting means for setting the length of a sample of said yarn which should be sent to the measuring zone of degree of entanglement(s) and the number of times that the needle should pierce the yarn within said sample length.

20. The apparatus of claim 19, wherein the setting means is a means capable of freely changing said sample length and said number of times that the needle should pierce the yarn.

* * * * *